United States Patent
Wu

(10) Patent No.: US 7,645,750 B2
(45) Date of Patent: Jan. 12, 2010

(54) METHOD OF TREATING SYMPTOMS OF HORMONAL VARIATIONS

(75) Inventor: Hung-Ming Wu, Taichung (TW)

(73) Assignee: Yung Shin Pharmaceutical Ind. Co., Ltd., Taichung (TW)

( * ) Notice: Subject to any disclaimer, the term of this patent is extended or adjusted under 35 U.S.C. 154(b) by 3 days.

(21) Appl. No.: 11/638,282

(22) Filed: Dec. 13, 2006

(65) Prior Publication Data

US 2008/0146541 A1  Jun. 19, 2008

(51) Int. Cl.
  A61K 31/56 (2006.01)
  A61K 31/55 (2006.01)
  A61K 31/519 (2006.01)
(52) U.S. Cl. .............. 514/177; 424/448; 514/217; 514/220; 514/259
(58) Field of Classification Search ............. 514/177, 514/217, 220, 259; 424/448
  See application file for complete search history.

(56) References Cited

U.S. PATENT DOCUMENTS

| 4,096,254 | A | 6/1978 | Benson et al. | |
|---|---|---|---|---|
| 4,499,019 | A | 2/1985 | Thominet et al. | |
| 6,297,243 | B1 | 10/2001 | Groendahl | |
| 6,310,098 | B1 | 10/2001 | Guttuso, Jr. | |
| 6,613,792 | B1 | 9/2003 | Ellenberger et al. | |
| 2005/0118242 | A1* | 6/2005 | Dudley et al. | 424/448 |
| 2005/0119248 | A1* | 6/2005 | Buntinx | 514/217 |
| 2005/0256112 | A1* | 11/2005 | Brodney et al. | 514/227.5 |
| 2006/0122127 | A1* | 6/2006 | Rao et al. | 514/23 |
| 2007/0264358 | A1* | 11/2007 | Wittlin | 424/722 |

FOREIGN PATENT DOCUMENTS

WO  WO 2004/004784 A1  1/2004
WO  WO 2006/051111 A1  5/2006

OTHER PUBLICATIONS

International Search Report for PCT/IB2007/004514, mailed Oct. 9, 2008.
Written Opinion of the International Searching Authority for PCT/IB2007/004514, mailed Oct. 9, 2008.
Chen, Yaqiong et al., "Changes of plasma serotonin precursor metabolite concentrations in postmenopausal women with hot flushes," Chin J. Obstet Gynecol, Dec. 2002, 37(12), p. 726-728.
Sipe, Kimberly et al., "Serotonin 2A receptors modulate tail-skin temperature in two rodent models of estrogen deficiency-related thermoregulatory dysfunction," Brain Research 1028 (2004) 191-202.
Casper et al., "Objective measurement of hot flushes associated with the premenstrual syndrome", Fertility Sterility, 2: 341-344, 1987.
Connolly, Moira, "Premenstrual syndrome: an update on definitions, diagnosis and management", Advances Psychiatric Treatment, 7: 469-477, 2001.
Grady, Deborah, "Management of Menopausal Symptoms", N. Engl. J. Med. 355: 2338-47, 2006.
Hahn et al., "Menopausal-like hot flashes reported in women of reproductive age", Fertility Sterility, 70: 913-918, 1998.
Suvanto-Luukonen et al., "Citalopram and fluoxetine in the treatment of postmenopausal symptoms: a prospective, randomized, 9-month, placebo-controlled, double-blind study", Menopause, 12: 18-26, 2005 (see Abstract).
Yonkers et al., "Premenstrual syndrome", Lancet, 371: 1200-1210, 2008.
Product Insert of Zyprexa by Lilly (Mar. 2009).
Product Insert of Clozaril by Novatis (Nov. 2004).

* cited by examiner

*Primary Examiner*—Ardin Marschel
*Assistant Examiner*—Zohreh Vakili
(74) *Attorney, Agent, or Firm*—Howrey LLP; Viola T. Kung

(57) ABSTRACT

A method for treating or preventing symptoms of hormonal variation includes administering an effective amount of a receptor antagonist to a subject having one or more symptoms of hormonal variations, wherein the receptor antagonist binds to at least one selected from the group consisting of a serotonin type 2A ($5\text{-}HT_{2A}$) and a dopamine type 2 ($D_2$) receptors.

19 Claims, No Drawings

METHOD OF TREATING SYMPTOMS OF HORMONAL VARIATIONS

BACKGROUND OF INVENTION

1. Field of the Invention

The present invention relates generally to treatment or prevention of symptoms of hormonal variation, such as hot flashes, night sweats, and insomnia.

2. Background Art

Hot flashes (also called vasomotor flashes) are the most common symptoms experienced by women who are perimenopausal or postmenopausal. A hot flash is a sudden sensation of warmth, which is usually accompanied by skin reddening, perspiration, palpitation, anxiety, irritability, and even panic, and night sweats. A chill may follow a hot flash because of a subsequent drop in core temperature. Hot flashes vary: they can be several times a week or once per hour, they can be characterized by mild warmth to profuse sweating, and they can last from several seconds to 60 minutes. Such symptoms can disrupt sleep and work and interfere with quality of life.

Almost 60-70% of postmenopausal women have hot flashes, and approximately 10-20% of all postmenopausal women will report intolerable symptoms, including hot flashes. Some women may suffer from these symptoms for up to 15 years (Kronenberg F. "Hot flashes: epidemiology and physiology," *Ann. N.Y. Acad. Sci.*, 592:52-86(1990)). Thus, the identification and proper management of menopausal symptoms are crucial to maintaining a woman's quality of life.

Typical hot flashes occur with sudden onsets of sensation of warmth in the chest, which then spreads upward to involve the neck and face. Hot flashes can last from a few seconds to several minutes. However, the severity of the sensations vary greatly both from time to time in the same woman and from woman to woman. Hot flashes may be accompanied by dizziness, nausea, headaches, palpitations, profuse sweating and night sweats. How often a woman experiences hot flashes also varies, ranging from many times a day to once a week or less. Such symptoms can disrupt sleep and work and interfere with quality of life. In some women, hot flashes are provoked by several factors such as hot weather, stress, eating, or drinking alcohol.

Although the pathophysiology of hot flashes is not completely understood, it has been postulated that hot flashes result from a transient lowering of the hypothalamic temperature regulatory set point (Stearns et al., "Hot flushes," *Lancet*, 360:1851-1861 (2002)). Because of the temporal relation between changes in sexual hormone concentrations and the onset of hot flashes, it is believed that such symptoms result from declining estrogen levels or increased gonadotropin concentrations. Thus, hot flashes occur commonly in menopausal women, but also in women taking anti-estrogen drugs, such as tamoxifen. Men on androgen deprivation treatment may also experience such symptoms.

Although estrogen replacement therapy can effectively minimize or prevent hot flashes in women, many women are concerned about potential risks of hormone replacement therapy. This is especially true for women who suffer from breast cancer or have a family history of breast cancer, and/or a history of clotting disorder (Col et al., "Patient-specific decisions about hormone replacement therapy in postmenopausal women," *JAMA*, 277; 1140-1147(1997); Gail et al., "The menopause," *Lancet*, 353:571-580 (1999)).

Various non-hormonal agents have been tested as well, such as clonidine. Clonidine is a centrally-acting $\alpha_2$ adrenergic receptor agonist. It selectively stimulates receptors in the brain that monitor catecholamine levels in the blood. These receptors close a negative feedback loop that begins with descending sympathetic nerves from the brain that control the production of catecholamines (e.g., epinephrine, also known as adrenaline, and norepinephrine) in the adrenal medulla. By tricking the brain into believing that catecholamine levels are higher than they really are, clonidine causes the brain to reduce its signals to the adrenal medulla, leading to lower catecholamine production. The result is a lowered heart rate and blood pressure. In randomized clinical trials, clonidine was shown to be moderately more efficacious than placebo (Goldberg et al., "Transdermal clonidine for ameliorating tamoxifen-induced hot flashes," *J. Clin. Oncol.*, 12:155-158 (1994); Pandya et al., "Oral clonidine in postmenopausal patients with breast cancer experiencing tamoxifen-induced hot flashes: a University of Rochester Cancer Center Community Clinical Oncology Program study," *Ann Intern Med.* 132:788-793 (2000)), but adverse effects are common, including dry mouth, dizziness, and blurred vision.

Recent randomized clinical trials also confirmed that some selective serotonin-reuptake inhibitors (SSRI), such as venlafaxine and paroxetine, are more effective than placebo in minimizing the occurrence and severity of hot flashes (Loprinzi et al., "Venlafaxine in management of hot flashes in survivors of breast cancer: a randomized controlled trial," *Lancet* 356:2059-2063 (2000); Stearns et al., "Paroxetine controlled release in the treatment of menopausal hot flashes: A randomized controlled trial," *JAMA* 289:2827-2834 (2003)). However, adverse effects with SSRIs are moderate, including headache, agitation, tremor, sedation, and sexual dysfunction.

Given the risks of estrogen replacement therapy and marginal benefits of current non-hormonal treatments, there is a continued need for alternative methods or drugs for treating or preventing symptoms associated with menopause, including hot flashes.

SUMMARY OF INVENTION

In one aspect, embodiments of the invention relate to methods for treating or preventing symptoms of hormonal variation. A method in accordance with one embodiment of the invention includes administering an effective amount of a receptor antagonist to a subject having one or more symptoms of hormonal variations, wherein the receptor antagonist binds to at least one selected from the group consisting of a serotonin type 2A (5-HT$_{2A}$) receptor and a dopamine type 2 (D$_2$) receptor. The receptor antagonist is one selected from risperidone, quetiapine, clozapine, olanzapine, aripiprazole, ziprasidone, zotepine, and 9-hydroxyrisperidone.

Other aspects and advantages of the invention will become apparent from the following description and attached claims.

DETAILED DESCRIPTION

Embodiments of the invention relate to methods for treating or preventing symptoms associated with hormonal variations, particularly those associated with hormonal changes accompanying menopause. In the following description, numerous details are set forth to provide an understanding of the present invention. However, it would be understood by those skilled in the art that the present invention may be practiced without these details and that numerous variations or modifications from the described embodiments are possible without departing from the scope of the invention. The methods of the invention may involve administering an effective amount of a therapeutic agents by oral administration, injection, inhalation, transdermal patch, or any other routes commonly used in the art.

Furthermore, the following describes several examples to illustrate embodiments of the invention. These examples are for illustrative purpose only. One of ordinary skill in the art would appreciate that these examples are not exhaustive and they are not intended to limit the scope of the invention. In addition, it should be understood that throughout this specification, when a concentration or amount range is described as being useful, or suitable, or the like, it is intended that any and every concentration or amount within the range, including the end points, is to be considered as having been stated. Furthermore, each numerical value should be read once as modified by the term "about" (unless already expressly so modified) and then read again as not to be so modified unless otherwise stated in context. For example, "a range of from 1 to 10" is to be read as indicating each and every possible number along the continuum between about 1 and about 10. In other words, when a certain range is expressed, even if only a few specific data points are explicitly identified or referred to within the range, or even when no data points are referred to within the range, it is to be understood that the inventors appreciate and understand that any and all data points within the range are to be considered to have been specified, and that the inventor have possession of the entire range and all points within the range.

Although menopause is a natural process that occurs in women's lives as part of normal aging. Some women go through these courses with few symptoms, while others have significant or even disabling symptoms such as hot flashes. Hot flashes are generally systemic and likely result from an alteration in the thermoregulatory set-point centre, which is located in the pre-optic anterior hypothalamus, with involvement of dopamine, serotonin, nor-epinephrine, and alpha-adrenergic receptors. (Steams et al., "Hot flushes," *Lancet* 360:1851-1861 (2002)).

Among various receptors, inventor of the present invention had found that specific subtypes of dopamine, serotonin, and a adrenergic receptors are effective targets for the treatment of hot flashes and other symptoms associated with hormonal variations. Specifically, $5\text{-}HT_{2A}$ antagonist and/or $D_2$ dopamine antagonist are found to be effective in reducing or eliminating symptoms associated with hormonal variations.

Thus, in accordance with some embodiments of the invention, a method for treating or preventing symptoms of hormonal variations may comprise the use of an effective amount of an antagonist of $5\text{-}HT_{2A}$ serotonin receptor and/or $D_2$ dopamine receptor. An effective amount of an antagonist that binds $5\text{-}HT_{2A}$ and/or $D_2$ receptors will depend on the mode of administration, frequency of administration, and the type of pharmaceutical composition used to deliver the compound into a patient, as well as weight, gender, age, and physical conditions of the patient. Generally, effective amounts of such compounds will be about 0.002 mg to about 0.5 mg/kg body weight per day, preferably about 0.005 mg to 0.1 mg/kg body weight per day, and more preferably about 0.005 to about 0.034 mg/kg body weight per day. For example, daily doses may range from about 0.1 to about 25 mg per day for an adult patient weighing about 50 Kg (110 lb), or from about 0.2 to about 50 mg per day for an adult patient weighing about 100 Kg (220 lb). While individual needs vary, determination of optimal range of effective amounts of each compound is within the skills of one skilled in the art. By treating the symptoms of hormonal variations, including hot flashes, embodiments of the invention either reduce the number (occurrence or frequency), duration, and/or severity of symptomatic events. Administering a compound of the invention to a patient may be via any suitable route used for administering similar pharmaceuticals to a patient, including oral administration, injection, and transdermal patch, to name a few. The compound may be administered with any pharmaceutically acceptable carrier or excipient.

Serotonin (5-HT) receptors comprise about 15 different receptors. Type 2 ($5\text{-}HT_2$) serotonin receptors are $G_q/G_{11}$ coupled receptors that mediate cellular effects by increasing cellular levels of inositol triphosphate ($IP_3$) and diacylglycerol (DAG). In accordance with some embodiments of the invention, serotonin type 2A receptor is the target for treating or preventing symptoms associated with hormonal variation. Rreduction in 5-HT levels increases the sensitivity of $5\text{-}HT_{2A}$ receptor in the hypothalamus, which is involved in thermoregulation. Therefore, modulators of $5\text{-}HT_{2A}$ receptors may be useful in the management of symptoms associated with hormone variations.

In accordance with one embodiment of the invention, risperidone may be used to treat symptoms of hormonal variations. Risperidone (Belivon®, Rispen®, Risperdal® in the United States) is an antipsychotic medication that functions by interfering with the communication among nerves in the brain. Risperidone acts as a $5\text{-}HT_{2A}$ antagonist and can be used to quickly and effectively block the effects of $5\text{-}HT_{2A}$ agonists at a low dose. Risperidone is also a potent dopamine type 2 ($D_2$), and $\alpha_2$ adrenergic receptor antagonist. Thus, risperidone has been used in the treatment of psychotic disorders, for example, schizophrenia. However, as described in the following sections, risperidone has been unexpectedly found to be effective in reducing or eliminating symptoms associated with hormonal variations.

In accordance with another embodiment of the invention, 9-hydroxyrisperidone may be used as a treatment for the symptoms of hormonal variations. 9-Hydroxyrisperidone is the principal active metabolite of risperidone, and they had similar binding profiles and affinity for $5\text{-}HT_{2A}$ receptors and $D_2$ receptors. (Leysen et al., "Risperidone: a novel antipsychotic with balanced serotonin-dopamine antagonism, receptor occupancy profile, and pharmacologic activity," *J Clin Psychiatry:* 55 Suppl: 5-12 (1994)). Like risperidone, 9-hydroxyrisperidone can effectively treat or prevent the symptoms associated with hormonal variations its antagonist activity for $5\text{-}HT_{2A}$ and/or dopamine receptors.

In addition to risperidone and 9-hydroxyrisperidone, other receptor antagonists that can bind to $5\text{-}HT_{2A}$ and/or $D_2$ dopamine receptors may also be used to control symptoms associated with hormonal variations. These other antagonists, for example, may include quetiapine, clozapine, olanzapine, aripiprazole, ziprasidone, and zotepine.

In accordance with another embodiment of the invention, quetiapine may be used as a treatment for the symptoms of hormonal variations. The antipsychotic effect of quetiapine is thought to be mediated by its antagonist activity against dopamine and 5-HT receptors. Specifically, dopamine receptors $D_1$, $D_2$, and 5-HT receptors, $5\text{-}HT_{1A}$ and $5\text{-}HT_2$ subtypes, are antagonized.

Serial PET scans evaluating the $D_2$ dopamine receptor occupancy of quetiapine have revealed that quetiapine rapidly disassociates from the $D_2$ receptor. Theoretically, this allows for normal physiological surges of dopamine to elicit their normal effects in areas such as the nigrostriatal and tuberoinfundibular pathways, thus minimizing the risk of side effects such as pseudo-Parkinsonism and elevations in prolactin. Quetiapine also has an antagonistic effect on the $H_1$ histamine receptor. This may be responsible for the sedative effect of the drug.

In accordance with some embodiments of the invention, clozapine may be used as a treatment for the symptoms of hormonal variations. Clozapine is classified as an 'atypical' antipsychotic drug because its profile of binding to dopamine receptors and its effects on various dopamine-mediated behaviors differ from those exhibited by more typical antipsychotics. In particular, clozapine has a high affinity for the D4 receptor and it also interferes to a lower extent with the binding of dopamine with $D_1$, $D_2$, $D_3$ and $D_5$ dopamine receptors. However, clozapine does not induce catalepsy, nor does it inhibit apomorphine-induced phenotype in animal models seen with 'conventional' neuroleptics. This evidence suggests that clozapine is preferentially more active at limbic than at striatal dopamine receptors and may explain its relatively mild extra-pyramidal side effects and its strong anti-cholinergic activity. Clozapine is also a strong antagonist of different subtypes of adrenergic, cholinergic, histaminergic and serotonergic receptors.

In accordance with some embodiments of the invention, olanzapine may be used as a treatment for symptoms of hormonal variations. Olanzapine is structurally similar to clozapine, and has a high affinity for dopamine and serotonin receptors. Olanzapine has a low affinity for histamine, cholinergic muscarinic and α-adrenergic receptors. The mechanism of action of olanzapine is unknown. However, it is thought that olanzapine's antipsychotic activity is mediated primarily by antagonism of dopamine receptors, specifically $D_2$ dopamine receptor. 5-HT antagonism may also play a role in the effectiveness of olanzapine. However, the significance of 5-$HT_{2A}$ antagonism is debated among researchers.

In accordance with some embodiments of the invention, aripiprazole may be used as a treatment of symptoms of hormonal variations. Aripiprazole (Abilify® from Bristol-Myers Squibb) is a new atypical antipsychotic medication awaiting approval by the FDA for the treatment of schizophrenia. Aripiprazole has been approved by the FDA for the treatment of acute manic and mixed episodes associated with bipolar disorder. Aripiprazole appears to mediate its antipsychotic effects primarily by acting as a partial agonist of the $D_2$ receptor. Partial agonism at $D_2$ receptors has been shown to modulate dopaminergic activity in areas where dopamine activity may be high or low, such as the mesolimbic and mesocortical areas of the schizophrenic brain, respectively. In addition to partial agonist activity of the $D_2$ receptor, aripiprazole is also a partial agonist of the 5-$HT_{1A}$ receptor. Like other atypical anti-psychotics, aripiprazole exhibits antagonist activities against the 5-$HT_{2A}$ receptor. Aripiprazole has moderate affinities for histamine and α-adrenergic receptors, but no appreciable affinity for cholinergic muscarinic receptors.

In accordance with some embodiments of the invention, ziprasidone may be used as a treatment of symptoms of hormonal variations. Ziprasidone has a high affinity for dopamine, serotonin, and alpha-adrenergic receptors and a moderate affinity for histaminic receptors. Ziprasidone is somewhat unique among the "atypicals" in that it can also inhibit synaptic reuptake of serotonin and norepinephrine, although the clinical significance of this is unknown. The mechanism of action of ziprasidone is unknown. However, it is thought that its antipsychotic activity is mediated primarily by its antagonism against dopamine receptors, specifically $D_2$ dopamine receptor. Serotonin antagonism may also play a role in the effectiveness of ziprasidone, but the significance of 5-$HT_{2A}$ antagonism of ziprasidone is debated among researchers. Antagonism at histaminic and alpha adrenergic receptors likely explains some of the side effects of ziprasidone, such as sedation and orthostasis.

In accordance with some embodiments of the invention, zotepine may be used as a treatment of symptoms of hormonal variations. Zotepine has a high affinity for the $D_1$ and $D_2$ dopamine receptors. It also affects the 5$HT_{2A}$, 5$HT_{2C}$, 5$HT_6$, and 5$HT_7$ receptors. In addition, it can also inhibit the reuptake of noradrenaline.

Clinical Examples

The following examples are provided to illustrate that embodiments of the present invention can reduce the symptoms of hormone variations, including hot flashes, night sweats, and blood pressure fluctuations. Embodiments of the invention are effective for patients under various conditions. However, one of ordinary skill in the art would appreciate that these examples are for illustration only and by no means are intended to limit the scope of the invention.

Embodiments of the invention involve administering a therapeutically effective amount of an antagonist (such as risperidone or 9-hydroxyrisperidone) of 5-$HT_{2A}$ and/or $D_2$ dopamine receptor to alleviate symptoms associated with hormone variations. For example, risperidone has been used on several patients to successfully alleviate the occurrence of hot flashes or other symptoms of hormonal variations. The following describe four specific examples from four different patients to illustrate the effectiveness of risperidone in alleviating symptoms associated with hormone variations. One of ordinary skill in the art would appreciate that these specific examples are not intended to limited the scope of the invention. For example, embodiments of the invention may use other regimens, including other antagonists of 5-$HT_{2A}$ and/or $D_2$ dopamine receptors.

Patient 1: Risperidone Resolved Hot Flashes in a Case with Hysterectomy

A 68-year-old woman was admitted to the hospital in December of 2004 due to hot flashes, hypertension, and restlessness. She had been told that she was suffering from essential hypertension for 16 years and had taken anti-hypertension medications for several years. However, her blood pressure still fluctuated and frequently dropped below critical level after taking sublingual adalate (10 mg) for sudden onsets of high blood pressure. She had no history of psychiatric or systemic diseases, except for a total abdominal hysterectomy at age 45. On admission, it was observed that her hot flash attacks occurred many times a day, lasting a few minutes and was usually followed by high blood pressure up to 180-200/84-96 mmHg, general shivers, and anxiety for 20-60 minutes. Such clinical symptoms started around age 50 and grew progressively worse.

Her biochemical and hematological results, such as sodium and potassium levels, 140 mmol/L and 4.0 mmol/L, respectively, were all within normal ranges. Plasma cortisol levels were within the normal range and showed diurnal rhythm. The plasma adrenaline, nor-adrenaline, VMA, epinephrine, and dopamine levels as well as thyroid hormones, including T3, T4, and TSH, were also normal. SSR and RRIV tests to assess sympathetic and parasympathetic functions, respectively, demonstrated her autonomic nervous system was normal. EEG showed no focal epileptiform discharges nor abnormal background activities. Brain MRI showed aging brain changes, but no lesion in hypothalamus or brain stem. 24-hour Holter's scan showed normal sinus rhythm. Echocardiography demonstrated normal cardiac chamber size, normal LV systolic performance, and wall motion.

After one month of observation, the patient received treatments of Premarin® 0.625 mg/day, Prozac® 20 mg/day and Tofranil 20 mg/day, each for 1-2 months with limited success. Because estrogen withdrawal may alter the thermoregulatory set-point located in the hypothalamus, a regimen of a 5-$HT_{2A}$ and/or D2 antagonist may provide an effective therapy for symptoms of hormonal variations, such as hot flashes. Thus, the patient was treated with risperidone (2 mg/day). After three days of treatment, her hot flashes reduced markedly to a frequency of once per 1-2 weeks. Associated symptoms, such as palpitation and anxiety, also improved significantly. Thereafter, the dosage of anti-hypertension drugs was reduced. With the patient's permission, risperidone therapy was discontinued and hot flashes reoccurred within 2-3 days after discontinuing the treatment. The symptoms were again alleviated 3-4 days after resuming risperidone treatment.

Patient 2: Risperidone Resolved Hot Flashes of Natural Menopause

Patient 2 was a 57-year-old woman who began developing intolerable hot flashes and night sweats after natural menopause that occurred seven years ago. Although she responded well to hormone replacement therapy (Premarin® 0.625 mg per day), she discontinued the therapy one year prior to this study because she was concerned about the potential risk of breast cancer. One month after discontinuing hormone replacement therapy, she developed hot flashes up to ten times per day, night sweats up to three times per night that disrupted her sleep, and headaches. The patient then sought neurological consultation. The patient also suffered from headaches twice per day and fluctuating blood pressure. Risperidone was started at a dose of 2 mg per day and the patient reported that the occurrence of hot flashes reduced markedly two days after starting risperidone treatment and was completely eliminated by day 7. In addition, she slept well and her blood pressure stabilized. To assess the relationship between risperidone therapy and the resolution of hot flashes, risperidone was tapered off over 2 days. The patient experienced hot flashes and night sweats again two days after risperidone treatment was completely discontinued. Risperidone 2 mg daily was resumed and the patient has not suffered another hot flash since.

Patient 3: Risperidone Resolved Hot Flashes in a Perimenopausal Case

Patient 3 was a 46-year-old woman who was diagnosed with perimenopause, based on increased levels of follicle-stimulating hormone, increased variability in menstrual cycle length, development of hot flashes, and insomnia. The patient had had these symptoms for two years. She responded well to estrogen therapy. Because of health risks, the patient discontinued estrogen treatment and sought supplementary therapy, such as soy isoflavones, but without success. Risperidone treatment (1 mg per night) was started. At that time, the patient was experiencing seven hot flashes per day. The patient reported that the frequency and intensity of her hot flashes were markedly reduced three days after starting risperidone therapy. With her permission, risperidone was tapered off over two days, and the hot flashes developed again three days later. After risperidone treatment (1 mg daily) was resumed, the patient no longer experienced hot flashes, and the quality of her sleep and her life improved. Three months later, the dosage of risperidone was decreased to 0.25 mg or less per day, and the patient's hot flashes were still markedly eliminated.

Patient 4: Risperidone Resolved Residual Hot Flashes in a Case with Hormone Replacement Therapy Patient 4 was a 56-year-old woman who had developed hot flashes, with a frequency of once per hour, palpitation, insomnia, headache, restlessness, and unstable blood pressure for over seven years. Initially, the patient visited a psychiatrist for her sleep disorder and a cardiovascular specialist for her high blood pressure. A year later, because of intolerable hot flashes and other menopausal symptoms, she received hormone replacement therapy (Divina®). Although her hot flashes were reduced to twice per day, headaches persisted and her blood pressure fluctuated from 180 to 210/110 to 90 mm Hg despite treatment with anti-hypertension drugs. The patient was started on risperidone treatment, 1 mg at bedtime for the first two days, followed by 2 mg per night, for residual hot flashes. The patient's hot flashes were completely eliminated three days after starting the risperidone therapy. Additionally, the patient was able to take hormone four times a day and discontinue the use of all anti-hypertension drugs because her blood pressure stabilized within the normal range.

The above data clearly show that risperidone or similar receptor antagonists are effective in alleviating the symptoms associated with hormonal variations, such as hot flashes and blood pressure fluctuations. It is also contemplated that administration of a compound of the invention for alleviating symptoms associated with hormonal variations may be carried out in combination with other suitable therapeutic treatments which are useful for treating symptoms of hormonal variations, including hot flashes.

While not intended to be bound by the mechanisms of how these receptor antagonists function to alleviate symptoms associated with hormonal variations, the inventor believes these drugs probably function by inhibiting 5-$HT_{2A}$ serotonin receptor, $D_2$ dopamine receptor, and/or $\alpha_1$-adrenergic receptor.

Menopause is a natural process that occurs in women's lives as part of normal aging. Approximately one-third of women experience few or no symptoms, while the remaining may have significant or even disabling symptoms such as severe hot flashes. Hot flashes are generally systemic and likely result from an alteration in the thermoregulatory set-point centre, which is located in the pre-optic anterior hypothalamus, with involvement of dopamine, serotonin, nor-epinephrine, and alpha-adrenergic receptors (Steams et al., "Hot flashes," *Lancet* 360; 1851-1861 (2002)).

Risperidone, a benzisoxazole derivative, is an atypical antipsychotic drug, which binds with high affinity to the serotonin type 2A 5-$HT_{2A}$, dopamine type 2 ($D_2$), and $\alpha_1$-adrenergic receptors. Risperidone binds with lower affinities to the $\alpha_2$-adrenergic and $H_1$ histamine receptors. Risperidone does not bind to $D_1$ dopamine receptors and has no affinity (when tested at concentrations >$10^{-5}$ M) for muscarinic cholinergic receptors. (Grant and Fitton, "Risperidone. A review of its pharmacology and therapeutic potential in the treatment of schizophrenia," *Drug*, 48:253-273 (1994); Ota et al., "Peripheral injection of risperidone, an atypical antipsychotic, alters the body weight gain of rats," *Clin Exp pharmacol. physiol.*, 29:980-989 (2002)).

Experimental data suggest that stimulation of 5-HT2 and dopamine receptors can increase body temperatures. For example, direct stimulation of 5-$HT_{2A}$ receptors can also induce hyperthermia in animal models, while administration of 5-$HT_{2A}$ antagonists can prevent hyperthermia in the animal model for serotonin syndrome. However, administration of 5-$HT_{1A}$ agonists to rodent or human leads to a reduction in core body temperature. These results suggest that the two 5-HT receptor subtypes, 5-$HT_{1A}$ and 5-$HT_{2A}$, are closely associated with body temperature control (Oether et al., "Involvement of 5-$HT_{1A}$ and 5-$HT_{1B}$ receptors for citalopram-induced hypothermia in the rat," *Psychopharmacology*, 154:429-434 (2001); Salmi and Ahlenius, "Evidence for functional interactions between $5\text{-}HT_{1A}$ and $5\text{-}HT_{2A}$ receptors in rat thermoregulatory mechanisms," *Pharmacol. Toxicol.*, 82:122-127 (1998)).

During menopause, a marked decline in sexual hormones, especially estrogen levels, may lead to a significant reduction in blood serotonin (5-HT) levels. The reduction in serotonin levels increases the sensitivity of the $5\text{-}HT_{2A}$ receptors in the hypothalamus (Berendsen H H, "The role of serotonin in hot flashes," *Maturiatas*, 36:155-164 (2000)). Thus, when an internal and an external stimulus, such as anxiety, induces the release of serotonin to stimulate the enhanced sensitivity $5\text{-}HT_{2A}$ receptors, the set-point for body temperature is changed and hot flashes occur.

Pulsatile luteinizing hormone (LH) secretion theory is another common explanation for the development of hot flashes because administration of LH-RH agonist can result in hot flashes. The dopaminergic system seems to be involved in both pulsatile LH secretion and hot flashes in post-menopausal women. Anti-dopaminergic drugs could act on the thermoregulatory nucleus to reduce hot flashes by directly decreasing adrenergic effects on the thermoregulatory nucleus, or indirectly through mechanisms such as the short-loop feedback exerted by hyperprolactinaemia on the tubero-infundibular dopamine neurons with a secondary dopamine-like activity, or by stimulating the opioid system (Melis G B et al., "Effects of the dopamine antagonist veralipride on hot flashes and luteinizing hormone secretion in postmenopausal somen," *Obstet. Gynecol.* 72:688-692 (1988); Wesel et al., Veralipride versus conjugated oestrogens: a double-blind study in the management of menopausal hot flashes," *Curr. Med. Res. Opin.*, 8:696-700 (1984)).

Risperidone has high affinities for $5\text{-}HT_{2A}$ and $D_2$ receptors. Risperidone can counteract enhancement of 5-HT activity as well as decrease nor-epinephrine activity in the anterior hypothalamus in the serotonin syndrome (Nisijima et al., "Risperidone counteracts lethality in an animal model of the serotonin syndrome," *Psychopharmacology* 150:9-14 (2000)). In addition, risperidone may elevate circulating prolactin levels in healthy subjects and schizophrenic patients (Markianos et al., "Neuroendocrine serotonergic and dopaminergic responsivity in male schizophrenic patients during treatment with neuroleptics and after switch to risperidone," *Psychopharmacology*, 157:55-59 (2001)). Risperidone can also reduce or prevent hot flashes through anti-dopaminergic effects on the loop of tuberoinfundibular dopamine neurons and on nor-epinephrine activity in the anterior hypothalamus.

Advantages of embodiments of the invention may include one or more of the following. Embodiments of the invention can provide compositions and methods for the treatment of the symptoms of hormonal variations including hot flashes and night sweats. Additionally, these methods and compositions can also achieve normalization of blood pressure and elimination/reduction of palpitations. Compositions of the invention may comprise a serotonin type 2A ($5\text{-}HT_{2A}$) receptor, dopamine type 2 ($D_2$) receptor, and/or $\alpha_1$-adrenergic receptor antagonist and can provide a plethora of treatment options for improving the quality of life of women experiencing the symptoms of hormonal variations.

While the invention has been described with respect to a limited number of embodiments, those skilled in the art will appreciate that other embodiments can be devised which do not depart from the scope of the invention as disclosed herein. Accordingly, the scope of the invention should be limited only by the attached claims.

What is claimed is:

1. A method for treating one or more symptoms of hormonal variation associated with perimenopause or postmenopause, comprising:
   administering an effective amount of risperidone and/or 9-hydroxyrisperidone to a subject having one or more symptoms of hormonal variation associated with perimenopause or postmenopause, wherein the symptoms are selected from the group consisting of hot flashes, palpitations, profuse sweating, and night sweats.

2. The method of claim 1, wherein the symptoms are hot flashes and/or night sweats.

3. The method of claim 1, wherein risperidone is administered.

4. The method of claim 3, wherein the effective amount of risperidone is from 0.1 to 50 mg per day for an adult patient.

5. The method of claim 3, wherein the effective amount of risperidone is from 0.1 to 20 mg per day for an adult patient.

6. The method of claim 3, wherein the effective amount of risperidone is from 0.1 to 6 mg per day for an adult patient.

7. The method of claim 3, wherein the effective amount of risperidone is from 0.1 to 2 mg per day for an adult patient.

8. The method of claim 1, wherein 9-hydroxyrisperidone is administered.

9. The method of claim 3, wherein the effective amount of risperidone is administered by using a pharmaceutically acceptable formulation.

10. The method of claim 9, wherein the pharmaceutically acceptable formulation is selected from the group consisting of oral formulation, injection formulation, inhalation formulation, and transdermal patch.

11. The method of claim 8, wherein the effective amount of 9-hydroxyrisperidone is from 0.1 to 50 mg per day for an adult patient.

12. The method of claim 8, wherein the effective amount of 9-hydroxyrisperidone is from 0.1 to 20 mg per day for an adult patient.

13. The method of claim 8, wherein the effective amount of 9-hydroxyrisperidone is from 0.1 to 6 mg per day for an adult patient.

14. The method of claim 8, wherein the effective amount of 9-hydroxyrisperidone is from 0.1 to 2 mg per day for an adult patient.

15. The method of claim 8, wherein the effective amount of 9-hydroxyrisperidone is administered by using a pharmaceutically acceptable formulation.

16. The method of claim 15, wherein the pharmaceutically acceptable formulation selected from the group consisting of oral formulation, injection formulation, inhalation formulation, and transdermal patch.

17. The method of claim 1, wherein a mixture of risperidone and 9-hydroxyrisperidone is administered.

18. A method for treating hot flashes or night sweats in a subject, comprising the steps of:
   identifying a subject suffering from hot flashes or night sweats, and administering an effective amount of risperidone and/or 9-hydroxyrisperidone to the subject.

19. The method according to claim 18, wherein risperidone is administered.

* * * * *